US005744733A

United States Patent [19]
Bridenbaugh et al.

[11] Patent Number: 5,744,733
[45] Date of Patent: Apr. 28, 1998

[54] METHOD FOR TESTING AND SCREENING ELECTRONIC AND PHOTONIC PACKAGES FOR HYDROGEN DAMAGE SUSCEPTIBILITY

[76] Inventors: Paul Michael Bridenbaugh, 22 Iroquois Trail, Somerville, N.J. 08876; Gustav Edward Derkits, Jr., 55 Holmes Oval, New Providence, N.J. 07974; Franklin Richard Nash, 1069 Canal Rd., Princeton, N.J. 08540

[21] Appl. No.: 831,583

[22] Filed: Apr. 9, 1997

[51] Int. Cl.$^6$ ................................................ G01N 17/00
[52] U.S. Cl. ................................................ 73/865.6; 374/57
[58] Field of Search ................................ 73/865.6; 374/57

[56] References Cited

U.S. PATENT DOCUMENTS

| | | | |
|---|---|---|---|
| 4,739,258 | 4/1988 | Schwarz | 374/57 X |
| 4,925,089 | 5/1990 | Chaparro et al. | 73/865.6 X |
| 5,307,018 | 4/1994 | Gadgil | 73/865.6 X |
| 5,318,361 | 6/1994 | Chase et al. | 73/865.6 X |
| 5,361,284 | 11/1994 | Baum et al. | 73/865.6 X |
| 5,450,018 | 9/1995 | Rieser et al. | 73/865.6 X |
| 5,503,006 | 4/1996 | Babaian-Kibala et al. | 73/865.6 X |
| 5,636,924 | 6/1997 | McCracken et al. | 73/865.6 X |
| 5,646,813 | 7/1997 | Jon et al. | 374/57 X |

FOREIGN PATENT DOCUMENTS

| | | |
|---|---|---|
| 58-2636 | 1/1983 | Japan . |
| 60-209139 | 10/1985 | Japan . |

*Primary Examiner*—George M. Dombroske
*Assistant Examiner*—Paul D. Amrozowicz

[57] ABSTRACT

The specification describes a test procedure for evaluating the susceptibility of electronic and photonic device packages to degradation effects caused by ambient hydrogen in the device package during the service life of the packaged device. The test procedure uses a hydrogen soak in which the subassembly parts are immersed in high concentrations of hydrogen gas at moderately elevated temperatures. The hydrogen gas is preferably diluted with an inert gas such as nitrogen or argon for safety in handling and processing. The test procedure can be used to screen components once their susceptibility to hydrogen attack has been established.

9 Claims, 1 Drawing Sheet

METHOD FOR TESTING AND SCREENING ELECTRONIC AND PHOTONIC PACKAGES FOR HYDROGEN DAMAGE SUSCEPTIBILITY

FIELD OF THE INVENTION

This invention relates to techniques for testing and screening components, typically electronic and electro-optic components and IC assemblies, to determine the degree of risk of these components to long term failure due to hydrogen corrosion.

BACKGROUND OF THE INVENTION

The adverse effects of hydrogen on metal parts and assemblies have been known for some time. Fatigue failure and dynamic stress failure in mechanical structures of titanium, for example, have been recognized as failures due to hydrogen embrittlement of metal structural or electrical members.

More recently, the role of hydrogen in electronic and photonic device failures has been under intensive study. The active devices are typically packaged in protective housings to prevent ambient elements, e.g. oxygen and water vapor, from degrading the sensitive components, e.g., ICs and lasers.

IC devices may be encapsulated in plastic. In some cases, however, moisture can penetrate the plastic, and in concert with elements in the plastic the moisture may degrade the performance and/or cause failure. For high reliability applications where replacement of the defective component is impossible or too costly, the preferred protection against moisture and oxygen is enclosure of the device (IC, laser, LED, APD, HEMT, MESFET, etc.) in a hermetic metal module. The module is typically baked under vacuum, backfilled with a benign gas such as nitrogen, and then sealed so that the final assembly is hermetic.

Hermeticity may, however, not only be inadequate to prevent failure, but in some instances may even accelerate failure, and substantially increase the probability of infant mortality, i.e., the occurrence of early failures after deployment by an end user. The failure-producing agent is hydrogen which is desorbed over time from the interior walls of the modules. Sources of hydrogen include the industry standard module materials, e.g., Invar and Kovar as well as ceramics such as AlSiC used with HCl. With the recognition that it is the module itself that is the source of hydrogen, efforts are underway to prevent hydrogen-induced failures.

In hybrid circuit technology, the use of titanium and titanium compounds, e.g. thin film Ti for resistors etc., invites problems with hydrogen contamination. Assemblies using zirconium and tantalum are also at risk. The degradation mechanism generally involves titanium hydride which readily forms with even small concentrations of hydrogen.

In hybrid circuits, and also in individual semiconductor integrated circuits, the presence of hydrogen in proximity to oxide passivating layers results in oxide reduction, increased moisture formed by the combination of oxygen and hydrogen, and finally possible failure. This understanding of the role of hydrogen was elusive since device analysis showed low hydrogen concentrations in devices that failed. It later became evident that significant amounts of hydrogen are consumed as the moisture level increases and the failure mechanism progresses.

For GaAs— and InP— based devices (e.g., HEMTs and MESFETs) employing the industry standard gate metallization structures (Ti—Pt—Au or Ti—Pd—Au) and incorporated in the industry standard ferrous alloy packaging materials (Kovar or Invar), desorbed molecular hydrogen has a deleterious impact on the RF and DC characteristics. The molecular hydrogen is converted to atomic hydrogen in the presence of catalysts such as Pt or Pd, or any of the other platinum-group metals (Ru, Rh, Os or Ir) and may be injected into the semiconductor. Affected properties of devices are the drain current, transconductance, and gain. The I-V characteristics for Ru and Ir contacts were observed to change drastically after exposure to hydrogen. The observed changes have been attributed to barrier height and leakage current changes.

In addition to the direct detrimental impact of hydrogen on device performance and reliability, hydrogen can also have adverse indirect impacts. For example, for lasers soldered to Ti—Pt—Au metallized submounts, hydrogen desorbed from the Kovar module walls can cause delamination of the submount metallization. The delamination can produce effective failure of the laser by an electrical short, or by blockage of the light output, or by a physical lifting of the laser chip that increases the thermal resistance and decreases the laser coupling to the optical fiber.

Efforts to address the problem of hydrogen outgassing include attempts to eliminate hydrogen from the piece parts themselves prior to manufacture. Essentially all the parts of the package, including the mechanical piece parts of the device assembly that are made of ferrous metal alloys have the potential for contributing hydrogen to the internal package environment. However, eliminating hydrogen from these sources met with limited success, since controlling hydrogen at the low concentration levels potentially harmful is difficult.

In view of the difficulty in eliminating the source of hydrogen from the package, it was proposed to "precondition" the package by accelerating the outgassing process prior to sealing the package. However, significant hydrogen outgassing still occurs after 1000 hours of thermal aging at 125° C. Increasing the rate of outgassing by increasing the temperature is an approach to the problem but is limited because of limitations in the thermal treatment of the sensitive device components in the package. For example, ferrous alloy materials such as Kovar are electroplated with Ni and Au, an industry standard scheme. Thermally aging a module prior to lidding can produce a diffusion of the Ni through the Au and a subsequent formation of nickel oxide on the gold surface, making wire bonding difficult.

Workers in the art are left with the conclusion that hydrogen, at concentration levels sufficient to cause reliability or performance problems in these devices, is omnipresent and essentially unavoidable. Although significant understanding of the hydrogen contamination problem has been gained, as evidenced by the foregoing discussion, the problem remains complex and essentially unsolved.

STATEMENT OF THE INVENTION

To date, most of the efforts in addressing the problem of hydrogen contamination in electronic and optoelectronic device packages have been directed toward eliminating the source of hydrogen contamination. We have approached the problem from another vantage point. Given that many devices and assemblies are susceptible to hydrogen contamination, and that there remains to date no effective way of predicting device failures from ubiquitous hydrogen, we have developed an empirical process for screening piece parts and components to determine the susceptibility of those parts to degradation and failure due to the presence of hydrogen. The availability of this technique allows the device designer to select parts that avoid the most serious degradation effects of hydrogen contamination. Briefly stated, the screening method uses elevated hydrogen partial pressure and temperature in combination to accelerate damage from hydrogen over that expected for normal exposure levels in electronic or optoelectronic packages. These acceleration factors are applied, controlled, and measured separately by using an apparatus incorporating a pressurized environment within a temperature controlled environment. We developed a parametric formula, including the exponent of the hydrogen partial pressure in the environment and the activation energy for hydrogen penetration or diffusion in the target device.

Furthermore, even when the applicability of a specific model cannot be verified, the incorporation of parts having known susceptibilities to H -induced failure allows this test method to be used in a comparative mode, providing a relative rating of one group of parts against others.

BRIEF DESCRIPTION OF THE DRAWING

The figure is a schematic representation of the test apparatus used to demonstrate the invention.

DETAILED DESCRIPTION

Figure 1:
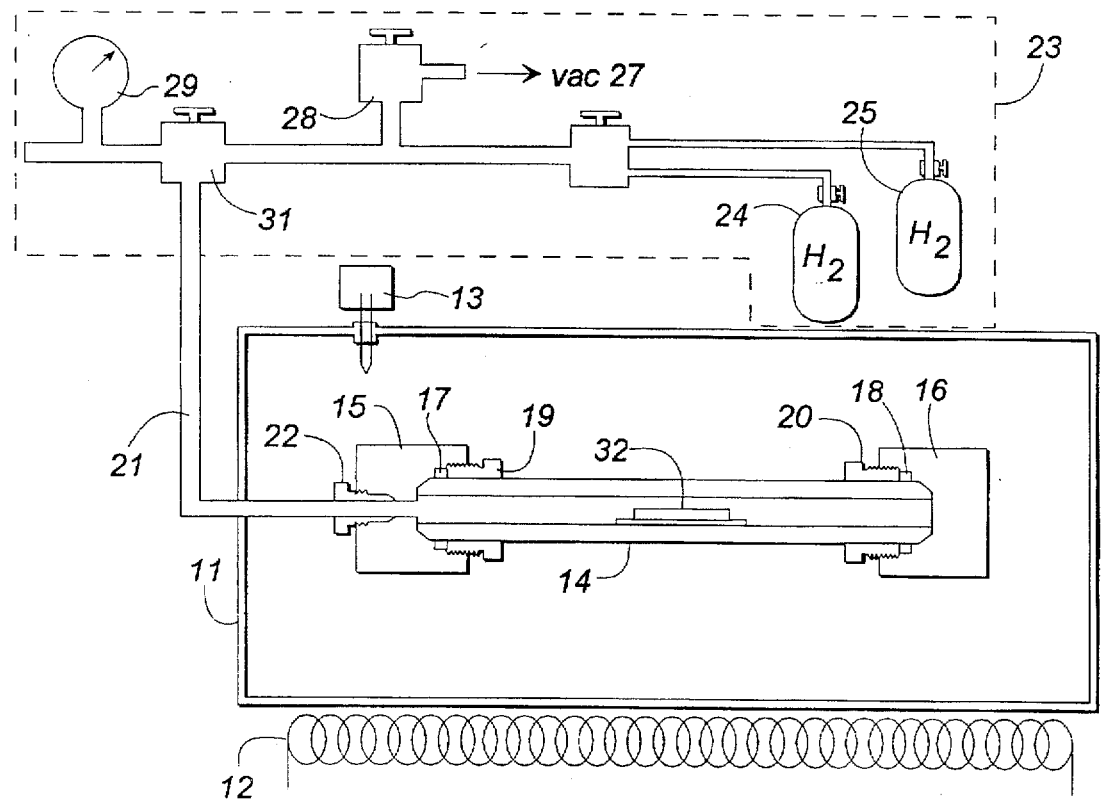

The following detailed embodiment of the invention is given by way of example and the specific procedures described were used to demonstrate the principle of the invention. The details are given to enable one to achieve the objective of the invention, but are in no way limiting with respect to the scope of the invention.

To develop the model for the generic screening process of the invention, we subjected selected piece parts, notably diamond and SiC laser device submounts, to a series of experiments using high hydrogen concentration ambients. The objective was to accelerate the hydrogen degradation process to a practical time frame for a commercial screening process. Elevated temperatures were also used in developing the model. However, temperature as an accelerating factor is limited by the sensitivity of the parts being tested to high temperature. The active components typically contained in the packages under test do not tolerate temperatures of more than a few hundred degrees C. At elevated temperatures the active impurity regions in the semiconductor devices degrade, and the metallization used for interconnects is oxidized. Differential thermal expansion of the materials in these packages at elevated temperatures also causes mechanical problems. Consequently an important feature of the test technique of the invention is to increase significantly the concentration of the hydrogen contaminant in the test ambient. Combining this expedient with the known accelerated thermal aging process provides an exceptionally reliable indication of the service life of the hermetically packaged components.

An apparatus suitable for carrying out the test procedure of the invention is shown in FIG. 1. In FIG. 1, oven 11 is shown with heating element represented schematically at 12. The temperature in the oven, and the temperature of the sample, is monitored using thermocouple 13. The test sample 32 is placed in a stainless steel autoclave 14 which controls the gas pressure and composition at the sample surface. The autoclave is supported and sealed by end caps 15 and 16 which are sealed to the autoclave with the aid of bushings 17 and 18, and threaded sealing plugs 19 and 20.

The gas inlet tube 21 is sealed to the autoclave by threaded plug 22. The gas ambient control system is shown generally at 23. The hydrogen degradation mechanism in the test is accelerated by using a very high concentration of hydrogen relative to the concentration in the service environment. However, hydrogen presents an explosion hazard when used in high concentrations. Thus we use a hydrogen gas mixture that is safe to handle but is still very high in hydrogen concentration from the standpoint of accelerating the hydrogen degradation mechanism. To meet these dual objectives we recommend a diluted hydrogen gas mixture of from 0.1–15% hydrogen by volume. The diluent in the gas mixture can be any of a number of gases such as nitrogen, helium or argon. It is preferable to avoid the choice of air as the diluent because of the potential for unwanted oxidation even at the modest temperatures used during the test procedure.

Referring again to FIG. 1, a source of hydrogen 24 and a source of nitrogen 25 are shown connected to the gas inlet tube 21 through mixing valve 26 and control valve 31. The vacuum source 27 and vacuum control valve 28 are used to purge the atmosphere in the autoclave prior to each test procedure. The pressure is monitored by gauge 29.

The test procedure involves placing the sample 32 in the autoclave, then purging the autoclave by pumping to a vacuum of $10^{-3}$ torr. The vacuum control valve 28 is closed and the autoclave backfilled with the hydrogen/nitrogen gas mixture from mixing valve 26. The pump down and backfill step can be repeated to assure the purity of the atmosphere in the autoclave. The furnace is then heated to the test temperature and the pressure within the autoclave rises to a pressure in the approximate range of 1–1000 atmospheres. The test duration will vary depending on the pressure and temperature chosen for the test procedure and the length of service life being simulated, and may range from a few hours to several days.

Materials that are potential contributors to hydrogen degradation and are used commonly in electronic and photonic device packages are ferrous alloys such as Kovar and Invar, particularly in combination with industry standard metallization systems that contain titanium such as Ti—Pt—Au. Other material systems capable of acting as sources for $H_2$ include ceramics such as AlSiC and reactive couples such as $H_2O$ or acids taken together with metals. The susceptible materials may comprise the active device, the interconnections for the device, or the packaging materials. For the purpose of this description all of these are considered "components".

The model developed in accordance with this invention to describe the time constant of hydrogen degradation τ is given by:
Equation (1)

$$\tau \alpha \frac{1}{P^\alpha} \exp\left(\frac{E}{kT}\right)$$

where P is the partial test pressure of the hydrogen, α is a pressure factor that depends in ways known to those skilled in the art on the degree of equilibrium of the gas phase surface interaction and lies in the range 0.5 to 1.0, (see Yuh Fukai, "Metal-Hydrogen System: Basic Bulk Properties", Springer Series in Materials Science 21, Springer-Verlag, New York 1993, ISBN # 3-540-55637-0). The activation energy E lies in the range 0.3 to 0.5 eV for metals such as gold or platinum (see Fukai text referenced above), k is the unique Boltzmann's Constant and T is the absolute test temperature. The partial test pressure is the product of the mole fraction of hydrogen and the absolute pressure. It is desirable to use a positive test pressure.

The following is an example of the use of the above equation.

EXAMPLE 1

Ceramic submounts are metallized with a standard submount coating comprising Ti and Pt. A laser is soldered to the submounts in known fashion. As is conventional in the art, to protect these devices from the ambient elements described above, the laser assemblies are enclosed in Invar hermetic packages. To test the device lifetimes a selected number of mounted lasers are oven tested according to the invention prior to hermetic packaging. These devices are sealed in the test apparatus described above and subjected to the accelerated hydrogen pressure test also as earlier described. The results of those tests are analyzed according to the following relationships.

The ratio of the time constant under test conditions ($\tau_t$) to the time constant under use conditions ($\tau_u$) is given by: Equation (2):

$$\frac{\tau_t}{\tau_u} = \left(\frac{P_u}{P_t}\right)^\alpha \exp\left[\frac{E}{k}\left(\frac{1}{T_t} - \frac{1}{T_u}\right)\right]$$

For this case, $\alpha=1$, $E=0.48$ eV and $k=0.862 \times 10^{-4}$ eV/K. The values of the test temperature, $T_t$, and the use temperature, $T_u$, are prescribed. In this example $T_t=150°$ C.$=423$K, and $T_u=30°$ C.$=303$K are chosen. The value of P, the partial test pressure of hydrogen, is known. By making up prototype modules and doing a gas analysis, the internal partial pressure under use conditions, $P_u$, can be determined. If the ratio of $P_u$ to $P_t$ is 1 to ten, then:

$$\tau_t = \tau_u \times 5.4 \times 10^{-4}$$

If the desired service lifetime for the component is 25 years, i.e. $2.2 \times 10^5$ hours, the test duration need only be 120 hours. To provide a margin of safety to account for variations in, for example, the hydrogen content of the hermetic modules and the use temperatures, the test duration can be increased. A factor of ten increase results in a test duration of 1200 hours, which is still a practical period.

Typically in a given lifetime test a series of test specimens is aged as above described to determine the point at which the test device degrades past an acceptable limit or fails. The indications of device degradation are well known to those skilled in the art and usually involve visible peeling or lifting of the metallization and changes in the device performance. The test time for the device to reach the failure criteria is termed here the test failure time $\tau_t$, and is used in the relationship given above for above for $\tau_t$ to estimate the service life $\tau_u$ of the device.

The clearly established fact is that both elevated temperatures and hydrogen pressures singly, or in concert, will accelerate hydrogen induced degradation mechanisms. In the event that the model of Equation (1) does not precisely apply to a given set of circumstances, the degradation acceleration strategy is still of considerable value in testing devices on a comparative basis. The only limits are those of the pressure vessel and the elevated temperatures the devices can tolerate in the absence of hydrogen.

The following is given by way of an example of a comparative test according to the invention.

EXAMPLE 2

SiC submounts metallized with Ti—Pt—Au were tested at 20 atmospheres in 15% Forming gas (15% $H_2$, 85% $N_2$) and 175° C. for 100 hours. The submounts showed no metal delamination. In contrast Ti—Pt—Au metallized diamond submounts showed extensive metal peeling after approximately four hours under the same conditions. The metallized SiC submounts were shown to be more robust than metallized diamond submounts against hydrogen attack using a test procedure of relatively short duration.

As this Example demonstrates, using the experience of multiple tests, including actual device failures under service conditions, control tests or standards can be developed which then allow further device testing to be done on a comparative basis. This allows a set of standard test lifetimes to be used against which new devices or new members of a category of devices can be measured. In developing the test conditions for a given hydrogen susceptibility test, it is preferred that at least two tests be conducted to calibrate the model described by Equation (1). In these tests two values are selected for at least one of the parameters P, T, or t. If parameter P is selected to be varied either the test pressure in the test chamber or the mole fraction of hydrogen can be used to vary P. The test failure time as defined above is then used in the model of equation (1) to determine the projected service life of the component. Alternatively, a test for a time period short of the test failure time can be used to determine a minimum service life for the component.

The testing procedures described here for measuring hydrogen susceptibility specify gas mixtures containing hydrogen as the test gas. The test gas can also be mixtures of deuterium or tritium in the same way as prescribed above for hydrogen. Deuterium may be used in preference to hydrogen because of its greater ease of detection in tests such as Secondary Ion Mass Spectroscopy (SIMS) and provides, thereby, a method for measuring hydrogen incorporation into the material to be tested, in cases where determination of damage due to hydrogenation may be difficult to measure. Similarly, tritium may be advantageously used to promote detectivity of hydrogenation by radiation detection, but is not preferred in most cases due to the associated radiation hazard.

Various additional modifications of this invention will occur to those skilled in the art. All deviations from the specific teachings of this specification that basically rely on the principles and their equivalents through which the art has been advanced are properly considered within the scope of the invention as described and claimed.

We claim:

1. A method for testing a component for susceptibility to hydrogen degradation comprising the steps of:
    (a) placing the component to be tested in a temperature controlled pressure vessel,
    (b) evacuating the pressure vessel,
    (c) backfilling the pressure vessel with a test gas mixture containing a critical gas selected from the group consisting of hydrogen, deuterium, and tritium and a diluent gas, thereby providing a partial pressure of said critical gas,
    (d) raising the ambient temperature of said pressure vessel to a predetermined test temperature T, thereby raising the partial pressure of said critical gas to a partial test pressure P,
    (e) allowing the component to remain in the pressure vessel at the test pressure P and predetermined test temperature T for a predetermined period,
    (f) cooling said pressure vessel,
    (g) releasing the pressure in the pressure vessel, and
    (h) examining the component to determine the extent of damage to the component caused by the hydrogen susceptibility test.

2. The test method of claim 1 in which the diluent gas is selected from the group consisting of argon, helium, nitrogen and mixtures thereof.

3. The test method of claim 1 in which the test parameters P, and T, are used to predict the service life of the component using the model:

$$\tau \propto \frac{1}{P^\alpha} \exp\left(\frac{E}{kT}\right)$$

where $\tau$ is the time constant of hydrogen degradation, P is the partial test pressure of the critical gas, $\alpha$ is a pressure factor in the range 0.5 to 1.0, E is the activation energy for the material being tested, k is Boltzmann's Constant, and T is the absolute test temperature.

4. The method of claim 3 in which the pressure factor is determined using a series of tests as defined in claim 1.

5. The method of claim 3 in which the service lifetime is determined using the relationship:

$$\frac{\tau_t}{\tau_u} = \left(\frac{P_u}{P_t}\right)^\alpha \exp\left[\frac{E}{k}\left(\frac{1}{T_t} - \frac{1}{T_u}\right)\right]$$

where $\tau_t$ is the test failure time, $\tau_u$ time constant of hydrogen degradation in service, $T_t$ is the test temperature, and $T_u$ is the service temperature.

6. The method of claim 3 in which $\alpha$ has a value of approximately 1.

7. The method of claim 3 in which the pressure in the pressure vessel is in the range 1–1000 atmospheres.

8. A method for testing a component for susceptibility to hydrogen degradation comprising the steps of:
(a) placing the component to be tested in a temperature controlled pressure vessel,
(b) evacuating the pressure vessel,
(c) backfilling the pressure vessel with a test gas mixture containing from 0.1 to 15% mole fraction of a critical gas selected from the group consisting of hydrogen, deuterium, and tritium and a diluent gas, thereby providing a partial pressure of said critical gas,
(d) raising the ambient temperature of said pressure vessel to a predetermined test temperature T, thereby raising the partial pressure of said critical gas to a partial test pressure P,
(e) allowing the component to remain in the pressure vessel at the test pressure P and predetermined test temperature T for a predetermined period,
(f) cooling said pressure vessel,
(g) releasing the pressure in the pressure vessel,
(h) examining the component to determine the extent of damage to the component caused by the hydrogen susceptibility test, and
(i) calculating the service life of the component being tested using the model:

$$\tau \propto \frac{1}{P^\alpha} \exp\left(\frac{E}{kT}\right)$$

where $\tau$ is the time constant of hydrogen degradation, P is the partial test pressure of the critical gas, $\alpha$ is a pressure factor in the range 0.5 to 1.0, E is the activation energy for the material being tested, k is Boltzmann's Constant, and T is the absolute test temperature.

9. The method of claim 8 wherein the test parameters P, T, and the test time for the test are selected using test results from a previous test using the same steps (a) to (i).

* * * * *